(12) United States Patent
Yamamoto

(10) Patent No.: US 10,894,130 B2
(45) Date of Patent: Jan. 19, 2021

(54) SYRINGE

(71) Applicant: DAICEL CORPORATION, Osaka (JP)

(72) Inventor: Yuzo Yamamoto, Hyogo (JP)

(73) Assignee: Daicel Corporation, Osaka (JP)

( * ) Notice: Subject to any disclaimer, the term of this patent is extended or adjusted under 35 U.S.C. 154(b) by 425 days.

(21) Appl. No.: 15/728,354

(22) Filed: Oct. 9, 2017

(65) Prior Publication Data

US 2018/0036486 A1 Feb. 8, 2018

Related U.S. Application Data

(63) Continuation of application No. PCT/CN2016/061087, filed on Apr. 5, 2016.

(30) Foreign Application Priority Data

Apr. 10, 2015 (JP) ................................. 2015-081260

(51) Int. Cl.
*A61M 5/315* (2006.01)
*A61J 1/20* (2006.01)
*A61M 5/30* (2006.01)

(52) U.S. Cl.
CPC ............ *A61M 5/315* (2013.01); *A61J 1/2096* (2013.01); *A61M 5/30* (2013.01); *A61M 5/31515* (2013.01); *A61M 2205/8231* (2013.01)

(58) Field of Classification Search
CPC .... A61M 5/315; A61M 5/30; A61M 5/31515; A61M 2205/8231; A61J 1/2096
See application file for complete search history.

(56) References Cited

U.S. PATENT DOCUMENTS 4,124,024 A * 11/1978 Schwebel ............... A61M 5/30
604/130
5,062,830 A  11/1991 Dunlap
(Continued)

FOREIGN PATENT DOCUMENTS

EP    1570875 A1    9/2005
JP    H10-512165 A  11/1998
(Continued)

OTHER PUBLICATIONS

Extended European Search Report dated Dec. 19, 2018 in related European Application No. 16776514.8.
(Continued)

*Primary Examiner* — Lauren P Farrar
(74) *Attorney, Agent, or Firm* — Knobbe Martens Olson & Bear LLP

(57) ABSTRACT

A syringe has a syringe main body, a syringe unit, and a piston. An end surface of the piston disposed on a forward end side is brought in contact with an end surface of a plunger disposed on a proximal end side so that the plunger is slidable toward a discharge port in a state in which a rod portion is accommodated in an accommodating hole in an attached state. In the attached state, the syringe unit is attached to the syringe main body, and a position of the plunger in a charging chamber is determined at a predetermined position at which an amount of an injection objective substance in the charging chamber is a predetermined amount on the basis of a position of the piston arranged in a through-hole of the syringe main body. Accordingly, the syringe is easily handled and the injection objective substance can be correctly charged.

13 Claims, 6 Drawing Sheets

(56) References Cited

U.S. PATENT DOCUMENTS

| | | | |
|---|---|---|---|
| 5,569,189 A | 10/1996 | Parsons | |
| 5,599,302 A * | 2/1997 | Lilley | A61M 5/30 604/135 |
| 5,643,211 A | 7/1997 | Sadowski et al. | |
| 8,133,494 B2 | 3/2012 | zur Megede et al. | |
| 2002/0169412 A1* | 11/2002 | Haar | A61M 5/30 604/70 |
| 2006/0281175 A1 | 12/2006 | McSwiggen et al. | |
| 2007/0021716 A1 | 1/2007 | Hansen | |
| 2008/0132450 A1 | 6/2008 | Lee et al. | |
| 2009/0099510 A1 | 4/2009 | Poulsen | |
| 2010/0040619 A1 | 2/2010 | Li et al. | |

FOREIGN PATENT DOCUMENTS

| | | |
|---|---|---|
| JP | H11-276585 A | 10/1999 |
| JP | 2001-505069 A | 4/2001 |
| JP | 2003-025950 A | 1/2003 |
| JP | 2005-523679 A | 8/2005 |
| JP | 2007-514489 A | 6/2007 |
| JP | 2007-525192 A | 9/2007 |
| JP | 2008-508881 A | 3/2008 |
| JP | 2008-206477 A | 9/2008 |
| JP | 2009-525094 A | 7/2009 |
| JP | 2010-503616 A | 2/2010 |
| JP | 2014-104112 A | 6/2014 |
| WO | WO 96/21482 A2 | 7/1996 |
| WO | WO 97/31665 A1 | 9/1997 |
| WO | WO 00/029050 A1 | 5/2000 |
| WO | WO 01/31282 A1 | 5/2001 |
| WO | WO 2005/058393 A2 | 6/2005 |
| WO | WO 2006/015373 A2 | 2/2006 |
| WO | WO 2007/088112 A1 | 8/2007 |

OTHER PUBLICATIONS

International Search Report dated Jul. 12, 2016 in International Application No. PCT/JP2016/061087, filed Apr. 5, 2016.
International Preliminary Report on Patentability dated Oct. 10, 2017 in corresponding International Application No. PCT/JP2016/061087.

* cited by examiner

SYRINGE

CROSS-REFERENCE TO RELATED APPLICATIONS

This application is a continuation application, and claims the benefit under 35 U.S.C. §§ 120 and 365 of PCT Application No. PCT/JP2016/061087, filed on Apr. 5, 2016, which is hereby incorporated by reference. PCT/JP2016/061087 also claimed priority to Japanese Patent Application No. 2015-081260 filed on Apr. 10, 2015, the entire contents of which are incorporated by reference.

TECHNICAL FIELD

The present disclosure relates to a syringe for injecting an injection objective substance into an injection target area.

BACKGROUND ART

An operation, in which an injection solution is charged into a syringe, is performed to prepare for the discharge or injection of the injection solution from the syringe. In relation thereto, Patent Literature 1 (Japanese Patent Application Laid-Open No. 11-276585) discloses a technique for charging an injection solution into an injection solution chamber. Specifically, a needleless syringe in Patent Literature 1 comprises a first grip (main body) GA which serves as a main body, a second grip GB which makes rotation and sliding movement with respect to the first grip GA, and a forward end nozzle which is detachable and which is screwed into a forward end of the first grip GA. The nozzle is formed with an injection solution chamber (cylinder chamber) for accommodating a sucked drug solution and a jet emission port (orifice). A piston is arranged in the injection solution chamber so that the piston can perform reciprocating sliding movement. The piston is connected to the second grip GB. When the injection solution is sucked, then the second grip GB is subjected to the rotation operation and the piston is pulled up to the proximal end side in a state in which the jet emission port is immersed in the injection solution.

Further, Patent Literature 2 (Japanese Translation of PCT International Application Publication No. 2007-514489) discloses a structure in which a negative pressure state is formed in a syringe by pulling a piston for pressurizing an injection solution upon the injection, and the injection solution is sucked through a nozzle into the syringe. In this procedure, in order to pull the piston more easily, a rod is provided, which extends from an end surface on a proximal end side of the piston. The user pulls the piston while gripping the rod. Further, Patent Literature 3 (Japanese Translation of PCT International Application Publication No. 2009-525094) also discloses a structure in which a rod is provided on an end surface on a proximal end side of a piston.

SUMMARY OF THE INVENTION

Problems to be Solved by the Invention

According to the conventional technique disclosed in Patent Literature 1 described above, the piston and the second grip GB are connected to one another by the aid of a piston rod. When the injection solution is sucked, it is necessary to pull up the piston to the proximal end side in accordance with the movement of the second grip GB screwed upwardly toward the proximal end side. Therefore, it is necessary to provide such a structure that the piston and the piston rod are not easily disengaged from each other. On this account, the nozzle is detachably attached to the forward end of the first grip GA, but it may be difficult to attach/detach the nozzle due to the presence of the piston.

Further, in the case of the conventional technique disclosed in Patent Literature 1 described above, the amount of the injection solution, which is sucked into the injection solution chamber, is adjusted by means of a scale marked on the grip. Therefore, it easily becomes difficult to charge a correct amount of the injection solution, on account of any erroneous reading. Further, nothing is suggested at all in relation to the charge of the correct amount of the injection solution in the conventional techniques disclosed in Patent Literatures 2 and 3.

Given the above-described problems, an object of the present disclosure is to provide such a syringe that the syringe is easily handled and an injection objective substance such as an injection solution or the like can be charged correctly.

Means for Solving the Problems

In order to solve the problems described above, in the present disclosure, when a syringe unit, which has a charging chamber for accommodating an injection solution, is attached to a syringe main body which has a piston, a plunger, which is slidable in the charging chamber, has a position which is determined on the basis of a position of the piston in accordance with the contact between the piston and the plunger. Accordingly, the amount of an injection objective substance accommodated in the charging chamber is automatically a predetermined amount in a state in which a syringe is finally formed. Therefore, a user can correctly prepare the predetermined amount of the injection objective substance in the syringe without performing any complicated operation. Note that in relation to the syringe according to the present disclosure, the term "forward end side" means the side on which a discharge port for discharging the injection objective substance from the syringe is arranged. The term "proximal end side" means the side which is opposite to the forward end side in the syringe. The terms do not refer to any specified place or position in any limited manner.

Specifically, the present disclosure resides in a syringe for injecting an injection objective substance into an injection target area; the syringe comprising a syringe main body which has a through-hole formed in an axial direction; a piston which is slidable in the through-hole; a syringe unit having a charging chamber which is capable of accommodating the injection objective substance, a plunger which is slidable in the charging chamber, and a nozzle portion which includes a flow passage having an inner diameter thinner than that of the charging chamber for allowing the injection objective substance contained in the charging chamber pressurized by sliding movement of the plunger to flow therethrough and which discharges the injection objective substance from a discharge port formed at a forward end of the flow passage, the syringe unit being attached to a forward end side of the syringe main body; and a driving unit which has an ignition device for combusting a powder and which applies, via the piston to the plunger, discharge energy for discharging the injection objective substance from the nozzle portion by the aid of a combustion product produced by the ignition device. Then, the plunger has a rod portion which extends toward the piston arranged in the through-hole of the syringe main body from an end surface disposed on a proximal end side in an attached state in which the syringe unit is attached to the syringe main body; and the syringe unit is formed so that the injection objective substance is charged into the charging chamber via the discharge port when the plunger is moved to the proximal end side by the aid of the rod portion in a state in which the plunger is arranged in the charging chamber. Further, an opening is provided on a forward end side of the piston so that the rod portion of the plunger can be inserted thereinto in the attached state, an accommodating hole is provided and formed so that an end portion of the rod portion disposed on the proximal end side is accommodated without making contact with the piston; an end surface of the piston disposed on the forward end side is brought in contact with the end surface of the plunger disposed on the proximal end side so that the plunger is slidable toward the discharge port in a state in which the rod portion is accommodated in the accommodating hole in the attached state, and a position of the plunger in the charging chamber is determined at a predetermined position at which an amount of the injection objective substance in the charging chamber is a predetermined amount on the basis of a position of the piston arranged in the through-hole.

In the syringe according to the present disclosure, the driving unit adopts, as the discharge energy, the combustion energy of the powder ignited by the ignition device. Note that when the combustion energy of the powder is utilized as the discharge or ejection energy, the powder may be, for example, any one of powders including a powder containing zirconium and potassium perchlorate, a powder containing titanium hydride and potassium perchlorate, a powder containing titanium and potassium perchlorate, a powder containing aluminum and potassium perchlorate, a powder containing aluminum and bismuth oxide, a powder containing aluminum and molybdenum oxide, a powder containing aluminum and copper oxide, and a powder containing aluminum and ferric oxide, or a powder composed of a combination of a plurality of powders described above. The feature of the powder as described above is as follows. That is, the combustion product thereof does not contain any gas component at the ordinary temperature even if the combustion product is a gas in a high temperature state. Therefore, the combustion product is immediately condensed after the ignition. As a result, when the syringe of the present disclosure is used for the injection into the living body, it is possible to efficiently perform the injection into a shallower portion of the injection target area of the living body. Further, when the energy generated by a gas generating agent is utilized as the discharge or ejection energy, it is also possible to use, as the gas generating agent, a single base smokeless powder and various gas generating agents used for a gas generator for the air bag and a gas generator for the seat belt pretensioner.

The discharge energy, which is applied by the driving unit, is transmitted to the plunger via the piston, and the plunger slides in the charging chamber. Accordingly, the injection objective substance, which is accommodated in the charging chamber, is extruded along the flow passage formed for the nozzle portion, and the injection objective substance is finally discharged or injected from the discharge port toward the injection target area. Note that, as for the syringe according to the present disclosure, the injection objective substance includes the component which is expected to exhibit the efficacy at the objective portion of the injection target area. Therefore, an accommodation state of the injection objective substance in the charging chamber and a specific physical form of the injection objective substance such fluid in a liquid or gel form, powder, granular solid is not particularly limited as long as that the discharge can be performed at least by the energy applied by the driving unit. For example, the injection objective substance may be a liquid.

Alternatively, the injection objective substance may be a solid in a gel form provided that the fluidity, which enables the discharge, is secured, even when the injection objective substance is the solid. The injection objective substance may contain a component which is to be delivered to the objective portion. The component may exist in a state of being dissolved in the injection objective substance or may exist in a simply mixed state without being dissolved. Examples of the component to be delivered include vaccines for enhancing antibody, proteins for cosmetic treatments, and cultured cells for regenerating hair. These components are contained in fluid in a liquid or gel form so that the components can be injected, whereby the injection objective substance is formed.

In this context, in the case of the syringe according to the present disclosure, the injection objective substance is not accommodated in the charging chamber from the beginning. When the user pulls the plunger toward the proximal end side by the aid of the rod portion provided on the proximal end side of the plunger in a state in which the plunger is arranged in the charging chamber, the interior of the charging chamber can be in the negative pressure state. Accordingly, the injection objective substance can be sucked into the charging chamber via the nozzle having the discharge port. In this way, when the structure, in which the charging operation is required to perform the charging into the charging chamber, is adopted, it is thereby possible to inject any arbitrary injection objective substance which is required. Therefore, in the case of the syringe according to the present disclosure, the syringe unit and the syringe main body are constructed to be detachable.

Therefore, it is preferable that the rod portion, which is provided for the plunger, has a shape and a size (length) required for the user to perform the charging operation described above. For example, the rod portion may have such a length that the end portion of the rod portion disposed on the proximal end side is disposed at a position at which the end portion protrudes from the interior of the charging chamber, in a state in which the plunger is disposed at the deepest position when the plunger arrives at the deepest side, i.e., the forward end side in the charging chamber.

Then, when the charging operation performed by the user is terminated, the rod portion, which is provided for the plunger, protrudes at the position corresponding to the amount of the injection objective substance charged in the charging chamber at that point in time. Then, in order to assemble the syringe, the syringe unit, which is in the state as described above, is attached to the syringe main body provided with the piston. In this arrangement, the piston is provided with the accommodating hole. The end portion of the rod portion of the plunger disposed on the proximal end side is accommodated in the accommodating hole of the piston in the attached state of the syringe unit without making contact with the bottom surface of the accommodating hole. However, the end surface of the plunger disposed on the proximal end side and the end surface of the piston disposed on the forward end side are brought in contact with each other. The force, which causes the sliding movement toward the discharge port, is applied to the plunger in accordance with the attachment. As a result, the plunger slides toward the forward end side up to a predetermined position on the basis of the position of the piston. Thus, the volume of the charging chamber is mechanically determined to be the predetermined amount. Note that the accommodating hole is not a through-hole which penetrates until arrival at the proximal end side of the piston.

That is, in the case of the syringe according to the present disclosure, in accordance with the attaching operation performed by the user for attaching the syringe unit and the syringe main body, the plunger, which is disposed on the side of the syringe unit, is always automatically adjusted to the specified position with respect to the piston disposed on the side of the syringe main body, i.e., the predetermined position described above at which the injection objective substance is in the predetermined amount. In this situation, the user merely performs the operation for assembling the syringe, and hence the operation is extremely easy. Further, the predetermined position of the plunger is unambiguously determined during the assembling of the syringe. Therefore, the accuracy of the metering of the injection objective substance is correct as well.

In this context, in the syringe as described above, the syringe main body may be provided with a movement regulating portion which regulates movement of the piston toward the proximal end side in the through-hole. In this case, the predetermined position relevant to the plunger is determined on the basis of a position determined by the movement regulating portion at which the piston can be moved most closely to the proximal end side in the through-hole. When the movement regulating portion is provided as described above, the piston can be reliably prevented from being moved in the through-hole of the syringe main body when the syringe unit is attached to the syringe main body. The position of the plunger, which is provided in the state of being attached as described above, can be precisely adjusted to the predetermined position.

In this context, two forms can be exemplified as examples of the movement regulating portion. In the first form, the syringe main body may be constructed to have a first main body portion which is positioned on the forward end side and a second main body portion which is positioned on the proximal end side. In this case, the first main body portion has therein a first through-hole which has a first predetermined diameter for allowing the piston to slide therein; and the second main body portion has therein a second through-hole which has a second predetermined diameter smaller than the first predetermined diameter for allowing a combustion product produced by the ignition device to arrive thereat. Then, a step, which serves as the movement regulating portion, is formed at a connecting portion between the first through-hole and the second through-hole when the syringe main body is formed by connecting the first main body portion and the second main body portion.

That is, in the first form, the first through-hole, in which the piston makes the sliding movement, has the diameter which is different from that of the second through-hole at which the combustion product arrives. Thus, the step is formed at the connecting portion between the first main body portion and the second main body portion. The presence of the step regulates the sliding movement of the piston toward the proximal end side. Note that it is not necessarily indispensable that the first through-hole and the second through-hole should be arranged coaxially. It is allowable that the relative positional relationship between the first through-hole and the second through-hole is any arbitrary relationship, provided that the combustion product arrives at the second through-hole, the energy, which is possessed by the arrived combustion product, is transmitted to the piston, the piston is slidable, and the step is formed. Further, the step may be formed in an annular form about the center of the axis of the syringe main body. Alternatively, it is not necessarily indispensable that the step should have any complete annular form, provided that the sliding movement of the piston toward the proximal end side is regulated.

In the next place, as for the second form, the ignition device may be arranged on the proximal end side of the syringe main body; and the movement regulating portion may be a cylindrical member which is arranged in the through-hole and which has an arrival space that extends in the axial direction so that the combustion product produced by the ignition device can arrive, an end portion of the cylindrical member disposed on the proximal end side being fixed to a portion at which the ignition device is arranged, and an end portion of the cylindrical member disposed on the forward end side being brought in contact with an end surface of the piston disposed on the proximal end side to thereby regulate movement of the piston toward the proximal end side. In this case, an opening of the arrival space disposed on the forward end side is covered with the end surface of the piston disposed on the proximal end side in a state in which the movement of the piston toward the proximal end side is regulated by the cylindrical member.

That is, in the second form, the proximal end side of the syringe main body, on which the ignition device is arranged, is used as the basis. The piston is specifically settled at the position separated therefrom by the length of the cylindrical member (the length is defined as the distance between the end portion of the cylindrical member disposed on the proximal end side and the end portion disposed on the forward end side), i.e., the movement thereof is regulated so that the piston is not moved from the concerning position toward the proximal end side. Note that the cylindrical member has the arrival space at the inside thereof. Therefore, the combustion product, which is produced by the ignition device, can arrive at the piston. Then, the energy, which is possessed by the combustion product, is transmitted to the piston via the opening of the arrival space disposed on the forward end side, and thus the piston undergoes the sliding movement. Note that the position, at which the movement of the piston toward the proximal end side is regulated, can be adjusted by changing the length of the cylindrical member. Thus, it is possible to adjust the predetermined position of the plunger. Specifically, the cross-sectional shape of the cylindrical member may be the same as the cross-sectional shape of the through-hole.

In this context, in the syringe as described above, the accommodating hole may have a contact portion which makes contact with a side surface of the rod portion in the state in which the rod portion is accommodated in the accommodating hole and a non-contact portion which does not make contact with the side surface of the rod portion; and a deep portion of the accommodating hole may be communicated with an opening of the accommodating hole via a gap formed between the non-contact portion and the rod portion in the state in which the rod portion is accommodated in the accommodating hole. When the rod portion is accommodated in the accommodating hole, then the contact portion makes contact with the side surface of the rod portion, and thus it is possible to enhance the integrality between the piston and the plunger. Upon the pressurization brought about by the combustion product, the combustion energy of the combustion product can be efficiently utilized for the pressurization of the injection objective substance. On the other hand, the non-contact portion is provided for the accommodating hole, and the deep portion of the accommodating hole is communicated with the opening. Accordingly, the rod portion is easily inserted into the accommodating hole. The positioning is precisely performed for the plunger to the predetermined position.

In this context, the syringe as described above may be constructed as follows. That is, the ignition device is an ignition device of an electric ignition type in which a powder is combusted by a supply current supplied from outside; and a syringe assembly, which is formed by the syringe main body, the piston, the syringe unit, and the driving unit, is detachably attached to a syringe housing which has a power source unit for supplying an ignition current to the ignition device. Then, in this case, it is preferable that an electric power supply terminal for the ignition device disposed on a side of the syringe assembly and an electric power supply terminal for the power source unit disposed on a side of the syringe housing are in a contact state when the syringe assembly is attached to the syringe housing. Owing to the structure as described above, it is extremely easy to assemble the syringe, and the convenience is improved for the user.

It is possible to provide such a syringe that the syringe is easily handled and the injection objective substance such as the injection solution or the like can be correctly charged.

EMBODIMENTS FOR CARRYING OUT THE INVENTION

An explanation will be made below with reference to the drawings about a syringe 1 according to an embodiment of the present disclosure. Note that the arrangement of the following embodiment is shown by way of example, and the present disclosure is not limited to the arrangement of the embodiment. Note that in this embodiment, the term "forward end side" and the term "proximal end side" are used as the terms for expressing the relative positional relationship in the longitudinal direction of the syringe 1. The term "forward end side" expresses the position deviated toward the forward end of the syringe 1 as described later on, i.e., deviated toward a discharge port 31a. The term "proximal end side" expresses the direction directed oppositely to the "forward end side" in the longitudinal direction of the syringe 1, i.e., the direction directed toward a driving unit 7.

First Embodiment

<Arrangement of Syringe 1>

Figure 1:
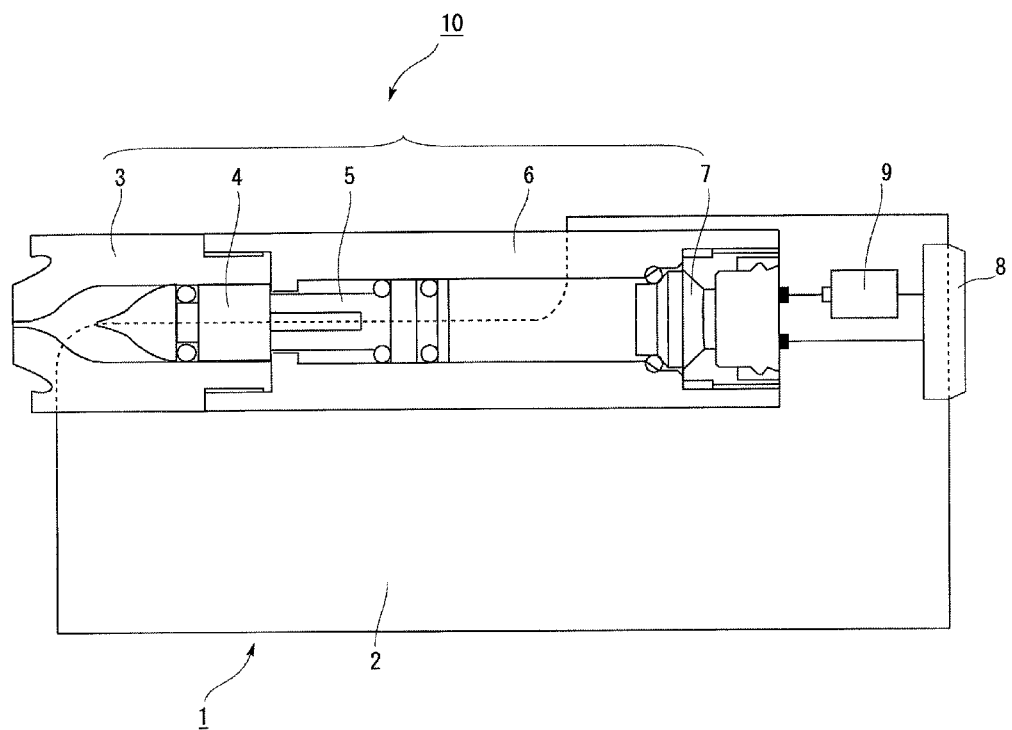
FIG. 1 shows a schematic structure of a syringe according to the present disclosure.

In this description, FIG. 1 shows a schematic structure of the syringe 1, which is also a sectional view taken in the longitudinal direction of the syringe 1. The syringe 1 is constructed such that a sub-assembly (see FIG. 3A described later on) constructed by a syringe unit 3 and a plunger 4 described later on and a sub-assembly (see FIG. 3B described later on) constructed by a syringe main body 6, a piston 5, and a driving unit 7 are assembled integrally into a syringe assembly 10 which is attached to a housing (syringe housing) 2. Note that in the following description of this specification, the injection objective substance, which is injected into an injection target area by the syringe 1, is generally referred to as "injection solution". However, this term does not intend to limit the content and the form of the substance to be injected. The component, which is to be delivered, for example, to a skin structure as the injection target area, may be either dissolved or not dissolved in the injection objective substance. Any specified form of the injection objective substance is available without any problem as well, for which various forms can be adopted, including, for example, liquid and gel forms, provided that the injection objective substance can be discharged to the injection target area from a discharge port 31a by being pressurized.

As described above, the syringe assembly 10 is constructed so that the syringe assembly 10 is detachable with respect to the housing 2. The injection solution is charged into a charging chamber 32 (see FIG. 3A) which is formed between the syringe unit 3 and the plunger 4 included in the syringe assembly 10. Then, the syringe assembly 10 is a unit which is disposable every time when the injection solution is discharged or injected. On the other hand, a battery 9, which supplies the electric power to an igniter 71 (see FIG. 2 described later on) included in the driving unit 7 of the syringe assembly 10, is included on the side of the housing 2. The electric power is supplied from the battery 9 via a wiring between an electrode disposed on the side of the housing 2 and an electrode disposed on the side of the driving unit 7 of the syringe assembly 10, in accordance with the operation performed by a user to depress a button 8 provided on the housing 2. Note that as for the electrode disposed on the side of the housing 2 and the electrode disposed on the side of the driving unit 7 of the syringe assembly 10, the shapes and the positions of the both electrodes are designed so that the electrodes are automatically brought in contact with each other when the syringe assembly 10 is attached to the housing 2. Further, the housing 2 is a unit which can be repeatedly used as long as the electric power, which can be supplied to the driving unit 7, remains in the battery 9. Note that if the electric power of the battery 9 is exhausted in the housing 2, it is also allowable that only the battery 9 is exchanged and the housing 2 is continuously used.

Figure 2:
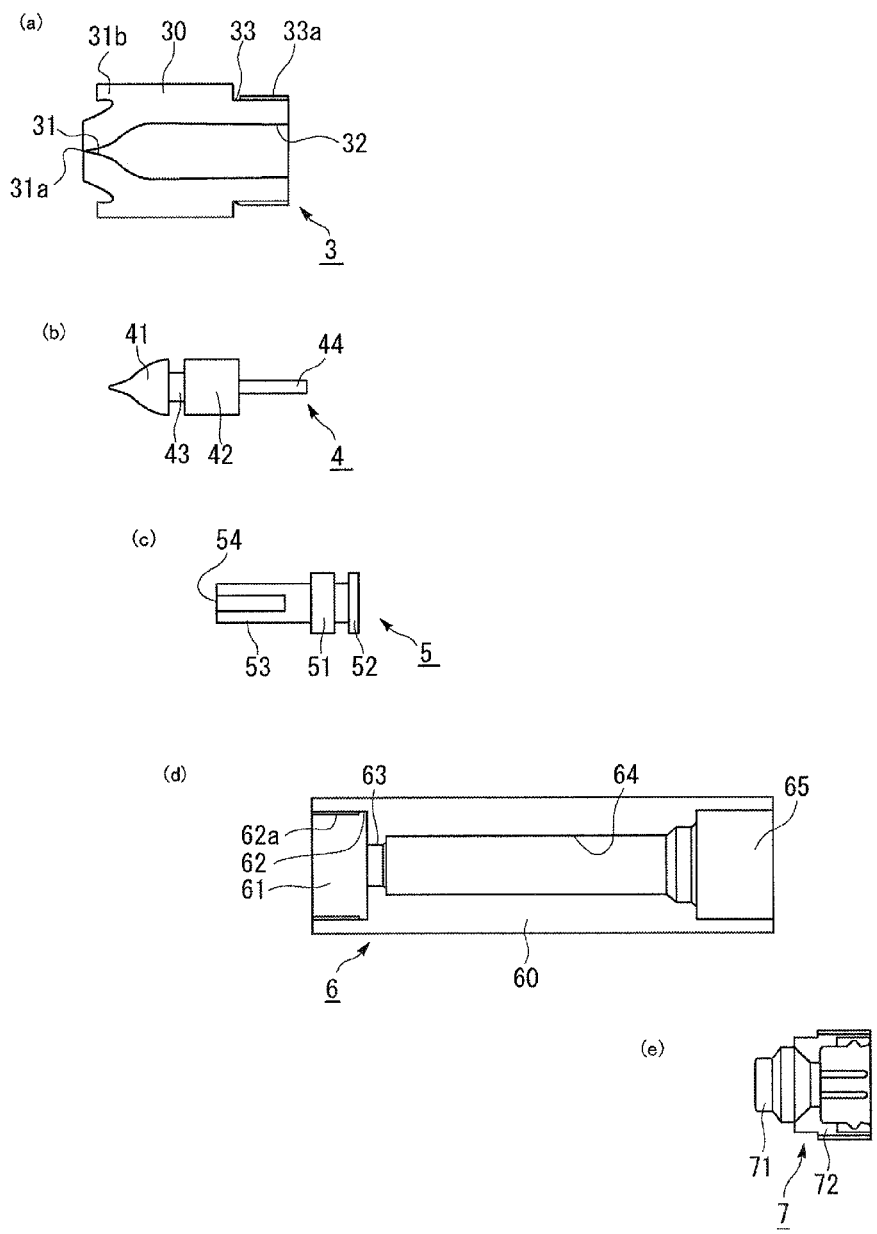
FIG. 2 shows schematic structures of a syringe unit (a), a plunger (b), a piston (c), a syringe main body (d), and a driving unit (e) for constructing a syringe assembly to be incorporated into the syringe shown in FIG. 1.

An explanation will now be made on the basis of FIG. 2 about detailed structures of the syringe unit 3, the plunger 4, the piston 5, the syringe main body 6, and the driving unit 7 for constructing the syringe assembly 10. (a) of FIG. 2 shows a structure of the syringe unit 3, and (b) of FIG. 2 shows a structure of the plunger 4. The syringe unit 3 has a nozzle portion 31 including the charging chamber 32 which is the space capable of accommodating the injection solution. Further, the plunger is arranged so that the plunger 4 is slidable in the charging chamber 32.

For example, as for a body 30 of the syringe unit 3, it is possible to use, for example, known nylon 6-12, polyarylate, polybutylene terephthalate, polyphenylene sulfide, or liquid crystal polymer. Further, it is also allowable that the resin as described above contains a filling material such as glass fiber, glass filler and the like. Polybutylene terephthalate may contain 20 to 80% by mass of glass fiber, polyphenylene sulfide may contain 20 to 80% by mass of glass fiber, and liquid crystal polymer may contain 20 to 80% by mass of mineral.

Then, the plunger 4 is arranged so that the plunger 4 is slidable in the direction of the nozzle portion 31 (direction directed toward the forward end side) in the charging chamber 32 formed at the inside of the body 30. The space, which is formed between the plunger 4 and the body of the syringe unit 3, is the space in which the injection solution is accommodated. In this arrangement, the plunger 4 slides in the charging chamber 32, and thus the injection solution, which is accommodated in the charging chamber 32, is pressed and discharged from the flow passage (discharge port 31a) provided on the forward end side of the nozzle portion 31. On this account, the plunger 4 is formed of a material with which the sliding movement is smoothly performed in the charging chamber 32 and the injection solution does not leak from the side of the plunger 4. Specifically, for example, butyl rubber and silicon rubber can be adopted as the material for the plunger 4. Further, examples of the material include styrene-based elastomer, hydrogenated styrene-based elastomer, and the styrene-based elastomer and the hydrogenated styrene-based elastomer added with polyethylene, polypropylene, polybutene, polyolefin such as α-olefin copolymer, liquid paraffin, oil such as process oil, and powder inorganic matters such as talc, cast, and mica. Further, polyvinyl chloride-based elastomer, olefin-based elastomer, polyester-based elastomer, polyamide-based elastomer, and polyurethane-based elastomer, various rubber materials (in particular, those subjected to vulcanization) such as natural rubber, isoprene rubber, chloroprene rubber, nitrile-butadiene rubber, and styrene-butadiene rubber, mixtures of the kinds of elastomer and the kinds of rubber, and the like can be adopted as the material for the plunger 4.

In this arrangement, as shown in (b) of FIG. 2, the plunger 4 has a head portion 41 and a body portion 42. The both are connected to one another by a neck portion 43 which has a diameter smaller than the diameters of the head portion 41 and the body portion 42. The reason, why the diameter of the neck portion 43 is small as described above, is that it is intended to form an accommodating space for an O-ring which serves as a seal member. Note that the contour of the head portion 41 on the forward end side has a shape which is approximately coincident with the contour of the inner wall surface of the nozzle portion 31. Accordingly, when the plunger 4 slides toward the nozzle portion 31 upon the discharge or injection of the injection solution, and the plunger 4 arrives at the deepest position positioned most deeply in the charging chamber 32, then the gap, which is formed between the plunger 4 and the inner wall surface of the nozzle portion 31, can be decreased as small as possible, and it is possible to suppress any useless consumption of the injection solution. However, the shape of the plunger 4 is not limited to any specific shape, provided that the desired effect is obtained with the syringe according to the present disclosure.

Further, the plunger 4 is provided with a rod portion which extends in the direction directed toward the proximal end side from the end surface of the body portion 42 disposed on the proximal end side. The diameter of the rod portion 44 is sufficiently smaller than that of the body portion 42. However, the rod portion 44 has the diameter which is to such an extent that the user can grip the rod portion 44 to cause the movement in the charging chamber 32. Further, the length of the rod portion 44 is determined so that the rod portion 44 protrudes from the end surface of the syringe unit 3 disposed on the proximal end side and the user can grip the rod portion 44, even when the plunger 4 is disposed at the deepest position (position disposed at the most forward end side) of the charging chamber 32 of the syringe unit 3.

The description will now return to an explanation about the syringe unit 3. The inner diameter of the flow passage provided for the nozzle portion 31 disposed on the side of the syringe unit 3 is formed to be thinner than the inner diameter of the charging chamber 32. Owing to the structure as described above, the injection solution, which is pressurized at a high pressure, is discharged or injected to the outside from the discharge port 31a of the flow passage. Thus, an annular shield portion 31b is provided to surround the surroundings of the discharge port 31a in the vicinity of the nozzle portion 31 on the forward end side of the syringe unit 3. For example, when the discharge port is pressed against the human skin to discharge the injection solution, it is possible to form the shield by means of the shield portion 31b so that the discharged injection solution is not scattered to the surroundings. Note that when the discharge port is pressed against the skin, the skin is recessed to some extent.

Accordingly, it is possible to enhance the contact performance between the discharge port and the skin, and it is possible to suppress the scattering of the injection solution. In view of the above, as shown in (a) of FIG. 2, it is also allowable that the forward end of the nozzle portion 31, at which the discharge port 31a is positioned, protrudes by a slight amount from the end surface of the shield portion 31b.

Further, a screw portion 33a, which is provided to connect the syringe main body 6 described later and the syringe unit 3, is formed on a neck portion 33 which is positioned on the proximal end side of the syringe unit 3. The diameter of the neck portion 33 is set to be smaller than the diameter of the body 30.

Next, an explanation will be made on the basis of (c) and (d) of FIG. 2 about the piston 5 and the syringe main body 6. The piston 5 is constructed such that the piston 5 is pressurized by the combustion product produced by the igniter 71 and the piston 5 slides in a through-hole 64 formed at the inside of a body 60 of the syringe main body 6. In this arrangement, the syringe main body 6 is formed with a connecting recess 61 disposed on the forward end side on the basis of the through-hole 64. The connecting recess 61 is the portion which is to be connected with the neck portion 33 of the syringe unit 3 described above. A screw portion 62a, which is screw-engageable with the screw portion 33a provided for the neck portion 33, is formed on a side wall surface 62 of the connecting recess 61. Further, the through-hole 64 and the connecting recess 61 are connected by a communication portion 63. However, the diameter of the communication portion 63 is set to be smaller than the diameter of the through-hole 64. Further, the syringe main body 6 is formed with a driving unit-accommodating recess 65 which is disposed on the proximal end side on the basis of the through-hole 64.

Further, the piston 5 is made of metal, and the piston 5 has a first body portion 51 and a second body portion 52. The piston 5 is arranged in the through-hole 64 so that the first body portion 51 is directed toward the connecting recess 61 and the second body portion 52 is directed toward the driving unit-accommodating recess 65. The piston 5 slides in the through-hole 64, while allowing the first body portion 51 and the second body portion 52 to be opposed to the inner wall surface of the through-hole 64 of the syringe main body 6. Note that the first body portion and the second body portion 52 are connected by a connecting portion which exists therebetween and which has a diameter thinner than those of the respective body portions. An O-ring or the like is arranged in the space which is formed between the both body portions as a result thereof, in order to enhance the tight contact performance with respect to the inner wall surface of the through-hole 64. Further, the piston 5 may be made of resin. In this case, metal may be used in combination for parts for which the heat resistance and the pressure resistance are required.

In this arrangement, a pressing column portion 53, which has the diameter smaller than the diameter of the first body portion 51 and smaller than the diameter of the communication portion 63 of the syringe main body 6, is provided at the end surface of the first body portion 51 disposed on the forward end side. The pressing column portion 53 is provided with an accommodating hole 54 which is open on the end surface disposed on the forward end side, which has the diameter that is not less than the diameter of the rod portion 44, and which has the depth that is deeper than the length of the rod portion 44. Therefore, when the piston 5 is pressurized by the combustion product brought about by the igniter 71, the pressing column portion 53 can transmit the pressurization energy to the end surface of the body portion 42 of the plunger 4 disposed on the proximal end side by the aid of the end surface disposed on the forward end side thereof. Note that the shape of the piston 5 is not limited to the shape shown in (c) of FIG. 2 as well.

Next, the driving unit 7 will be explained on the basis of (e) of FIG. 2. The driving unit 7 has a body 72 thereof which is formed to have a cylindrical shape. The driving unit 7 has therein the igniter 71 which is an electric type igniter for generating the energy for the discharge by combusting the powder component. The driving unit 7 is attached to the driving unit-accommodating recess 65 of the syringe main body 6 so that the energy generated by the igniter 71 can be transmitted to the second body portion 52 of the piston 5. In particular, the body of the driving unit 7 may be obtained by fixing a injection-molded resin to a metal collar. Any known method can be used for the injection molding. The body 72 of the driving unit 7 is formed of the resin material which is the same as the resin material of the body 30 of the syringe unit 3.

In this case, the powder used in the igniter 71 is preferably exemplified by a powder containing zirconium and potassium perchlorate (ZPP), a powder containing titanium hydride and potassium perchlorate (THPP), a powder containing titanium and potassium perchlorate (TiPP), a powder containing aluminum and potassium perchlorate (APP), a powder containing aluminum and bismuth oxide (ABO), a powder containing aluminum and molybdenum oxide (AMO), a powder containing aluminum and copper oxide (ACO), a powder containing aluminum and ferric oxide (AFO), and a mixture of some of the aforementioned powders. The powders as described above have the following characteristics. That is, the plasma at a high temperature and a high pressure is generated during the combustion immediately after the ignition. However, when the temperature becomes the ordinary temperature, and the combustion product is condensed, then the generated pressure is suddenly lowered, because no gas component is contained. It is also allowable that any powder other than the above is used as the powder, provided that the appropriate injection can be performed.

Further, any additional powder component is not specifically arranged in the syringe main body 6 shown in FIG. 1. However, in order to adjust the pressure transition applied to the injection solution by the aid of the piston 5, a gas generating agent or the like, which is combusted by the combustion product produced by the combustion of the powder in the igniter 71 and which produces the gas, can be also arranged in the igniter 71 and/or the through-hole 64 of the syringe main body 6. The construction, in which the gas generating agent is arranged in the igniter 71, is an already known technique as disclosed, for example, in International Publication No. 01-031282 and Japanese Patent Application Laid-Open No. 2003-25950. Further, an example of the gas generating agent is exemplified by a single base smokeless powder composed of 98% by mass of nitrocellulose, 0.8% by mass of diphenylamine, and 1.2% by mass of potassium sulfate. Further, it is also possible to use a variety of gas generating agents used for a gas generator for the air bag and a gas generator for the seat belt pretensioner. It is possible to change the combustion completion time of the gas generating agent by adjusting the dimension, the size, and the shape, especially the surface shape of the gas generating agent arranged in the through-hole 64. Accordingly, the pressure transition to be applied to the injection solution can be a desired transition, i.e., a transition with which the injection solution can appropriately arrive at the injection target area. In the present disclosure, the gas generating agent or the like, which is optionally used, is also included in the driving unit 7.

<Assembling of Syringe 1>

Figure 3A:
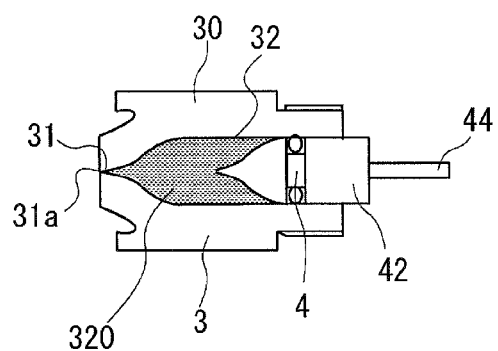
FIG. 3A shows a state in which the plunger is attached to the syringe unit shown in FIG. 2, and an injection solution is charged into a charging chamber.

An explanation will now be made about the assembling procedure for the syringe assembly 10 on the basis of FIGS. 3A to 3C. FIG. 3A discloses the sub-assembly constructed by the syringe unit 3 and the plunger 4. The sub-assembly is formed by inserting the plunger 4 into the charging chamber 32 of the syringe unit 3. Then, with the sub-assembly, the discharge port 31a is immersed in a container which is filled with the injection solution in a state in which the plunger 4 is inserted until arrival at the deepest portion. The plunger 4 is pulled while maintaining this state so that the plunger 4 returns to the side of the opening of the charging chamber 32, i.e., to the proximal end side of the syringe unit 3. In this situation, the negative pressure state is given in the charging chamber 32. Therefore, the injection solution enters the charging chamber 32 from the discharge port 31a to provide a state in which the charging chamber 32 is filled with the injection solution 320. Note that in this situation, the plunger 4 is pulled out until arrival at a position at which the end surface of the body portion 42 of the plunger 4 disposed on the proximal end side slightly protrudes from the end surface of the syringe unit 3 disposed on the proximal end side. The amount of the injection solution 320 contained in the charging chamber 32 is not necessarily a constant amount, depending on the pulling out amount of the plunger 4 pulled out by the user.

Figure 3B:
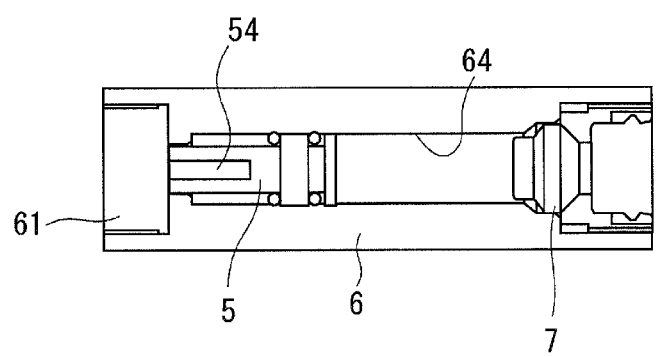
FIG. 3B shows a state in which the piston and the driving unit are attached to the syringe main body shown in FIG. 2.

In the next place, FIG. 3B discloses the sub-assembly constructed by the syringe main body 6, the piston 5, and the driving unit 7. As for this sub-assembly, the piston 5 is firstly inserted from the proximal end side of the syringe main body 6 shown in (d) of FIG. 2. In this procedure, the piston 5 is inserted into the through-hole so that the pressing column portion 53 is directed toward the connecting recess 61. Then, the positioning is performed to provide a state in which the end surface of the piston 5 disposed on the forward end side, i.e., the end surface of the pressing column portion 53 disposed on the forward end side, on which the accommodating hole 54 is open, protrudes by a predetermined amount from the bottom surface of the connecting recess 61 (surface orthogonal to the side wall surface 62). As for the positioning of the piston 5, any known technique may be appropriately utilized, for example, such that a mark for the positioning is set in the through-hole 64 and/or a jig for the positioning is used. Then, the driving unit 7 is attached to the driving unit-accommodating recess 65. Note that the fixing force for the piston 5 in the through-hole 64 is to such an extent that the piston 5 can slide in the through-hole 64 sufficiently smoothly in accordance with the pressure received from the combustion product brought about by the igniter 71 of the driving unit 7, and the fixing force is to such an extent that the piston 5 sufficiently resists against the force received from the plunger 4 and the position of the piston 5 does not vary when the sub-assembly shown in FIG. 3A is assembled to the sub-assembly shown in FIG. 3B as described later on.

Then, the sub-assembly shown in FIG. 3A is attached to the sub-assembly shown in FIG. 3B, and thus the syringe assembly 10 is formed. The process of formation is shown in FIG. 3C. At first, when the both sub-assemblies are attached, as shown in (a) of FIG. 3C, the neck portion 33 of the syringe unit 3 is fitted into the connecting recess 61 of the syringe main body 6 in a state in which the rod portion 44 of the plunger 4 is directed to the side of the piston 5. Then, the syringe unit 3 and the syringe main body 6 are connected to one another by screw-engaging the screw portions 33a, 62a. In this situation, when the both are progressively connected to one another, the rod portion 44 of the plunger 4 progressively enters the accommodating hole 54 provided for the pressing column portion 53 of the piston 5 to provide an accommodated state. Finally, such a state is given that the end surface of the pressing column portion 53 disposed on the forward end side is brought in contact with the end surface of the body portion 42 of the plunger 4 disposed on the proximal end side (state shown in (b) of FIG. 3C). Note that the accommodating hole 54 has the sufficient size to accommodate the rod portion 44. Therefore, in the contact state, the deep inner wall surface of the accommodating hole 54 (especially the bottom surface of the accommodating hole 54) is not brought in contact with the end portion of the rod portion 44 disposed on the proximal end side. Therefore, the rod portion 44 does not receive the load from the side of the piston 5.

Figure 3C:
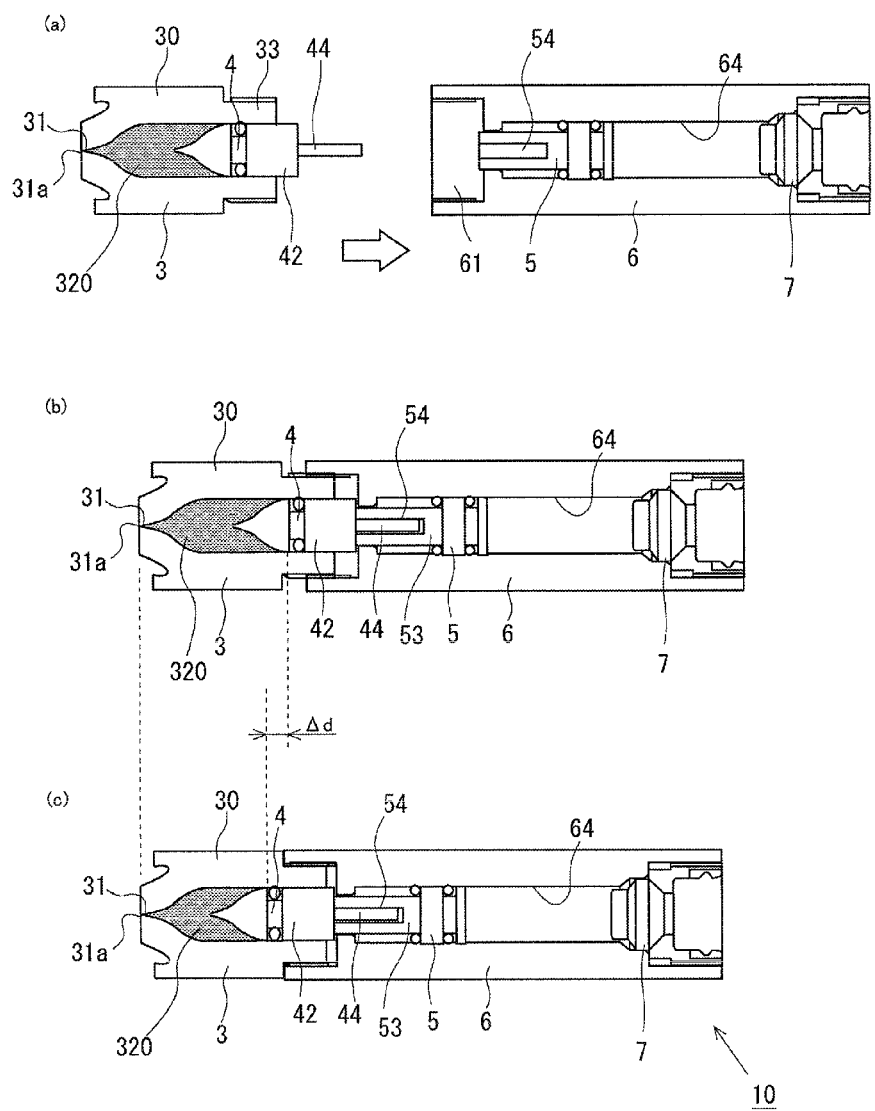
FIG. 3C shows a flow in which the syringe unit and the plunger shown in FIG. 3A are attached to the syringe main body, the piston, and the driving unit shown in FIG. 3B to form the syringe assembly.

Further, when the screw engagement between the syringe unit 3 and the syringe main body 6 is progressively advanced until arrival at the final screw engagement position while maintaining the contact state between the pressing column portion 53 and the body portion 42, then the plunger 4 is pushed by the pressing column portion 53 so that the plunger 4 advances toward the discharge port 31a, and the plunger 4 arrives at a state shown in (c) of FIG. 3C, because the position of the piston 5 is fixed with respect to the through-hole 64 by means of the sufficient friction force as described above. Note that as shown in FIG. 3C, the plunger 4 is pushed by Δd from the beginning of the contact between the pressing column portion 53 and the body portion 42 until arrival at the final screw engagement position shown in FIG. 3C. The plunger 4 is pushed as described above, and thus a part of the injection solution 320 contained in the charging chamber 32 is discharged from the discharge port 31a.

The pressing column portion 53 and the body portion 42 arrive at the final screw engagement position, and thus the formation of the syringe assembly 10 is completed. In the syringe assembly 10, such a state is given that the piston 5 is positioned at the predetermined position with respect to the syringe main body 6. The position of the plunger 4 is finally determined mechanically in the charging chamber 32 of the syringe unit 3 on the basis of the piston 5. The final position of the plunger 4 is the position which is unambiguously determined in the syringe assembly 10. Therefore, the amount of the injection solution 320 finally accommodated in the charging chamber 32 can be a previously determined predetermined amount.

As described above, in the syringe assembly 10, the user merely connects the sub-assemblies shown in FIGS. 3A and 3B to one another after performing the suction of the injection solution with the syringe unit 3 shown in FIG. 3A. For example, an operation, in which the injection solution is correctly measured, is not required in the series of assembling operations. However, in the case of the syringe assembly 10, the amount of the injection solution charged into the charging chamber is correctly the predetermined amount, although the strict measurement of the injection solution amount is not required for the user. Then, the syringe assembly 10 is attached to the housing 2, and the button 8 is depressed by the user in a state in which the discharge port 31a is brought in contact with the injection target area. Accordingly, the injection solution 320 is pressurized by the aid of the piston 5 and the plunger 4, and the discharge or injection of the injection solution 320 is executed. Note that the end portion of the rod portion 44 is not brought in contact with the inner wall surface in the accommodating hole 54. Therefore, no load is applied to the rod portion 44 during the pressurization caused by the igniter 71. Any breakage of the rod portion 44 is sufficiently avoided. As described above, in the case of the syringe 1, it is possible to realize the discharge of the injection solution in the correct amount, although the handling is extremely easy.

Second Embodiment

Figure 4:
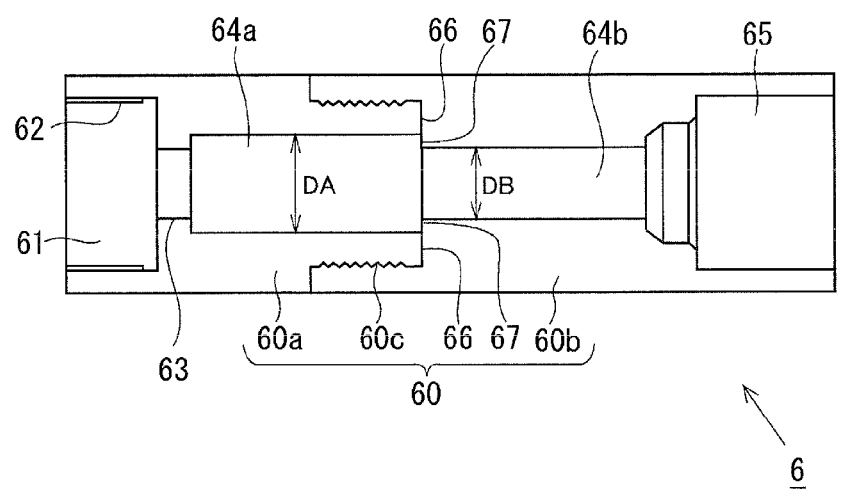
FIG. 4 shows a schematic structure of a syringe main body according to a second embodiment.

An explanation will be made on the basis of FIG. 4 about a second embodiment of the syringe 1. FIG. 4 shows a schematic structure of a syringe main body 6 according to this embodiment. Note that the constitutive components, which are the same as those of the syringe main body 6 shown in FIG. 2, are designated by the same reference numerals, any detailed explanation of which will be omitted. In this embodiment, a body 60 is formed so that the body 60 can be divided into a first body (first main body portion) 60a and a second body (second main body portion) 60b. The connecting recess 61 is formed on the side of the first body 60a, and the driving unit-accommodating recess 65 is formed on the side of the second body 60b. Then, the first body 60a and the second body 60b are screw-engaged and fastened by connecting portions 60c provided for the both to form the syringe main body 6. Further, the first body 60a is provided with a first through-hole 64a in which the piston 5 is slidably accommodated. The second body 60b is provided with a second through-hole 64b to serve as the space at which the combustion product brought about by the igniter 71 can arrive.

In this arrangement, the first through-hole 64a and the second through-hole 64b are in such a state that the central axes of the both holes are coincident with each other in a state in which the syringe main body 6 is formed. Then, the diameter DA of the first through-hole 64a is set to be larger than the diameter DB of the second through-hole 64b. Therefore, a step is formed by an end surface 66 of the first body 60a disposed on the proximal end side and an end surface 67 of the second body 60b disposed on the forward end side. As for the step, the end surface 67 is higher in the direction directed to the center of the through-hole. Therefore, when the piston 5 is accommodated in the first through-hole 64a, the movement of the piston 5 toward the proximal end side is regulated by the step caught by the piston 5.

In the case of the syringe 1 which utilizes the syringe main body 6 constructed as described above, when the piston 5 is incorporated into the syringe main body 6, the piston 5 is inserted into the first through-hole 64a in a state in which the body 60 is divided into the first body 60a and the second body 60b. In this procedure, the piston 5 is inserted into the first through-hole 64a so that the pressing column portion 53 of the piston 5 is directed toward the connecting recess 61. After that, the second body 60b is screw-engaged with the first body 60a in a state in which the piston 5 is inserted into the first body 60a. Further, the driving unit 7 is attached to the driving unit-accommodating recess 65. Note that in this embodiment, the fixing force for the piston 5 in the first through-hole 64a may be to such an extent that the piston 5 can slide in the through-hole 64 sufficiently smoothly in accordance with the pressure received from the combustion product brought about by the igniter 71 of the driving unit 7.

Then, the sub-assembly shown in FIG. 3A is attached to the sub-assembly formed by incorporating the piston 5 into the syringe main body 6 as described above, and thus the syringe assembly 10 is formed. In this situation, the rod portion 44 of the plunger 4 is accommodated in the accommodating hole 54 of the piston 5, and the pressing column portion 53 of the piston 5 is brought in contact with the body portion 42 of the plunger 4. The piston 5 is pushed toward the proximal end side in the first through-hole 64a by the force received from the plunger 4. However, in this embodiment, the movement of the piston 5 toward the proximal end side is regulated by the step described above (step formed by the end surfaces 66, 67). Then, the piston 5 is formed to provide such a state that the end surface of the pressing column portion 53 disposed on the forward end side protrudes by a predetermined amount from the bottom surface of the connecting recess 61 (surface orthogonal to the side wall surface 62) in the regulated state, in the same manner as the embodiment described above. As a result, the position of the plunger 4 is mechanically determined in the syringe unit 3 on the basis of the position of the piston 5 in the syringe main body 6 in the state in which the syringe assembly 10 is formed. Thus, the amount of the injection solution 320 finally accommodated in the charging chamber 32 can be the previously determined predetermined amount.

Third Embodiment

Figure 5:
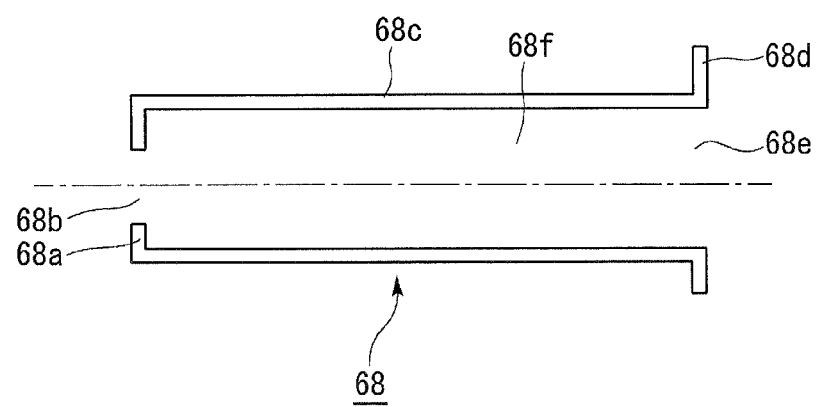
FIG. 5 shows a schematic structure of a cylindrical member used for a syringe according to a third embodiment.
Figure 6:
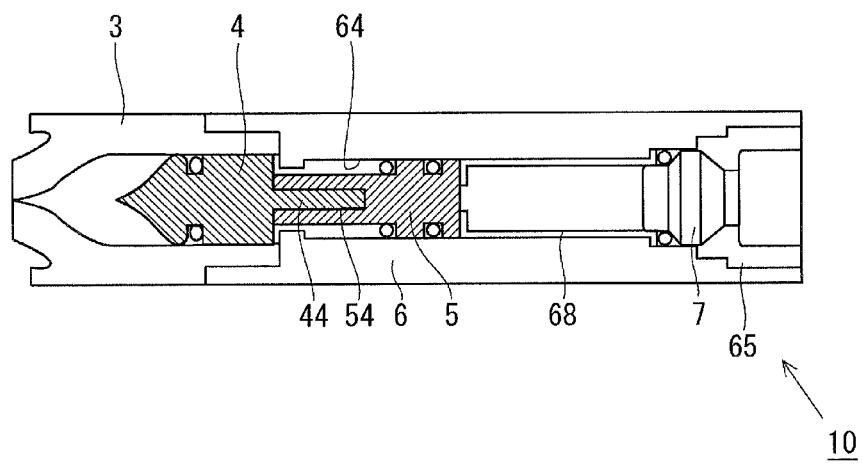
FIG. 6 shows a schematic structure of a syringe assembly formed by using the cylindrical member shown in FIG. 5.

An explanation will be made on the basis of FIGS. 5 and 6 about a third embodiment of the syringe 1. FIG. 5 shows a schematic structure of a cylindrical member 68 used for a syringe 1 according to this embodiment. FIG. 6 shows a schematic structure of a syringe assembly 10 formed by using the cylindrical member 68. Note that in FIGS. 5 and 6 the constitutive components, which are the same as those of the syringe assembly 10 described above, are designated by the same reference numerals, any detailed explanation of which will be omitted. This embodiment is different from the first embodiment in that this embodiment adopts such a structure that the movement of the piston 5 toward the proximal end side is regulated by the cylindrical member 68. The other features of this embodiment are substantially the same as those of the first embodiment.

FIG. 5 shows a cross section of the cylindrical member 68. The cylindrical member 68 has an opening 68b which is disposed on the forward end side, and the cylindrical member 68 has an opening 68e which is disposed on the proximal end side. Further, the cylindrical member 68 has a side portion 68c having an outer diameter which is approximately the same as the inner diameter of the through-hole 64. The space, which is formed by being surrounded by the side portion 68c, is an internal space (arrival space) 68f of the cylindrical member 68. A protrusion 68a, which rises in a slight amount from the side portion 68c toward the internal space 68f, is formed on the forward end side. The opening 68b is formed by the circumferential edge of the protrusion 68a. A brim portion 68d, which extends from the side portion 68c on the side opposite to the internal space 68f, is provided on the proximal end side.

The cylindrical member 68 constructed as described above is arranged in the syringe main body 6 in a state in which the brim portion 68d is caught by the step of the driving unit-accommodating recess 65 after the piston 5 is inserted into the through-hole 64 of the syringe main body 6. Further, the driving unit 7 is attached to the driving unit-accommodating recess 65, and the sub-assembly on the side of the syringe main body 6 is formed. As a result, the protrusion 68a of the cylindrical member 68 is positioned in the syringe main body 6 on the basis of the driving unit-accommodating recess 65. In this situation, it is also allowable that the protrusion 68a is not brought in contact with the piston 5.

Then, the sub-assembly shown in FIG. 3A is attached to the sub-assembly which is formed by incorporating the piston 5 into the syringe main body 6 as described above, and thus the syringe assembly 10 is formed. In this situation, the rod portion 44 of the plunger 4 is accommodated in the accommodating hole 54 of the piston 5, and the pressing column portion 53 of the piston 5 is brought in contact with the body portion 42 of the plunger 4. The piston 5 is pushed toward the proximal end side in the through-hole 64 by the force received from the plunger 4. However, in this embodiment, the movement of the piston toward the proximal end side is regulated by the protrusion 68a of the cylindrical member 68. Then, the piston 5 is formed such that the end surface of the pressing column portion 53 disposed on the forward end side is in a state of protrusion by a predetermined amount from the bottom surface of the connecting recess 61 (surface orthogonal to the side wall surface 62) in the regulated state, in the same manner as the embodiment described above. As a result, the position of the plunger 4 is mechanically determined in the syringe unit 3 on the basis of the position of the piston 5 in the syringe main body 6 in the state in which the syringe assembly 10 is formed. Thus, the amount of the injection solution 320 finally accommodated in the charging chamber 32 can be the previously determined predetermined amount.

Note that when the syringe assembly 10 is attached to the syringe 1 and the igniter 71 is driven, then the combustion product, which is brought about by the igniter 71, enters the internal space 68f from the opening 68e of the cylindrical member 68, and the combustion product passes through the opening 68b to press the piston 5. Further, the position of the piston 5 can be adjusted in the syringe assembly 10 by changing the length of the side portion 68c of the cylindrical member 68, i.e., the distance between the brim portion 68*d* and the protrusion 68*a*. As a result, it is possible to adjust the predetermined amount of the injection solution 320 finally accommodated in the charging chamber 32.

Fourth Embodiment

Figure 7:
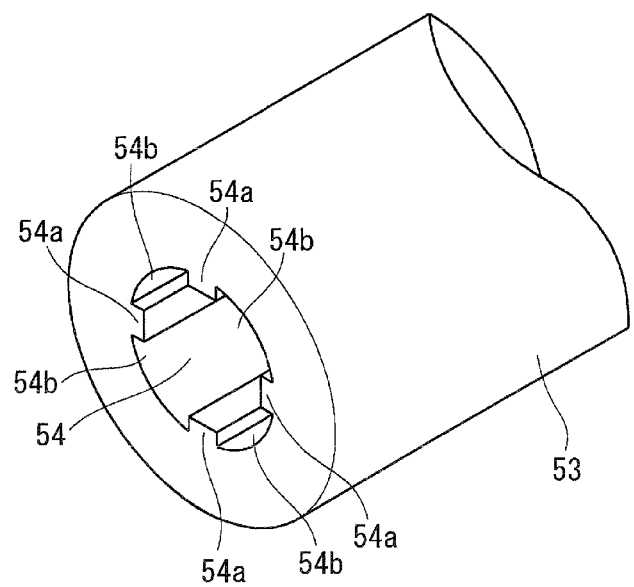
FIG. 7 shows a schematic structure of a piston according to a fourth embodiment.

An explanation will be made on the basis of FIG. 7 about a fourth embodiment of the syringe 1. FIG. 7 shows a schematic structure of a piston 5, especially a pressing column portion 53 according to this embodiment. In this embodiment, the accommodating hole 54 is formed with contact portions 54*a* which make contact with the side surface of the rod portion 44 in a state in which the rod portion 44 is inserted into the accommodating hole 54 and non-contact portions 54*b* which do not make contact with the side surface of the rod portion 44. Specifically, the contact portion 54*a* is a protruding portion which protrudes inwardly from the inner circumferential surface as viewed in a cross section of the accommodating hole 54 and which extends in the axial direction of the accommodating hole 54. The number of the contact portions 54*a* formed for the accommodating hole 54 is at least two, but the number is not limited to any specified number. Therefore, the rod portion 44 is progressively inserted into the accommodating hole 54, while maintaining a state in which parts of the side surface of the rod portion 44 are brought in contact with the contact portions 54*a*. Note that the end portion of the rod portion 44 disposed on the proximal end side is not brought in contact with the deep inner wall surface of the accommodating hole 54 (or the bottom surface of the accommodating hole 54) even in a state in which the rod portion 44 is entirely accommodated in the accommodating hole 54, in the same manner as the embodiment described above. Then, the deep portion of the accommodating hole 54 is connected to the opening of the accommodating hole 54 via the non-contact portions 54*b*.

In this way, when the rod portion 44 is inserted into the accommodating hole 54, then the contact portions 54*a* are brought in contact with the side surface of the rod portion 44, and thus it is possible to enhance the integrality between the piston 5 and the plunger 4. The combustion energy of the combustion product can be efficiently transmitted to the injection solution upon the pressurization brought about by the combustion product coming from the igniter 71. On the other hand, the non-contact portions 54*b* are provided for the accommodating hole 54, and the deep portion of the accommodating hole 54 is communicated with the opening of the accommodating hole 54. Accordingly, the rod portion 44 is easily inserted into the accommodating hole 54. It is possible to precisely perform the positioning of the plunger 4 in the syringe assembly 10.

Other Embodiments

According to the syringe 1 of the present disclosure, for example, cultured cells, stem cells, and the like may be seeded or inoculated into injection target cells or scaffold tissues (scaffolds) in the field of the regenerative medicine of human, in addition to the case where the injection solution is injected into the skin structure. For example, as described in Japanese Patent Application Publication No. 2008-206477, the syringe 1 may inject cells which may be appropriately determined by those skilled in the art depending on a transplantation portion and the purpose of the cell regeneration, for example, endothelial cells, endothelial precursor cells, myeloid cells, preosteoblast, chondrocytes, fibroblast, skin cells, muscle cells, liver cells, kidney cells, intestinal tract cells, and stem cells, as well as all cells considered in the field of the regenerative medicine.

Further, the syringe 1 of the present disclosure may be also used for delivering DNA or the like to cells or scaffold tissues (scaffolds) as described in Japanese Translation of PCT International Application Publication No. 2007-525192. In this case, it is possible to suppress an adverse effect on cells themselves or scaffold tissues (scaffolds) themselves when the syringe 1 of the present disclosure is used, as compared with when the delivery is performed using a needle. Therefore, it can be said that the use of the syringe 1 is more desirable.

Further, the syringe 1 of the present disclosure is ideally useful, for example, when various genes, cancer inhibiting cells, lipid envelops, and the like are directly delivered to target tissues and when antigen genes are administered to enhance the immunity against pathogens. In addition to the above, the syringe 1 can be also used, for example, in the field of medical treatment for various diseases (for example, see Japanese Translation of PCT International Application Publication Nos. 2008-508881 and 2010-503616) and the field of immunological medical treatment (for example, see Japanese Translation of PCT International Application Publication No. 2005-523679). The field, in which the syringe 1 is usable, is not intentionally limited.

The invention claimed is:

1. A syringe for injecting an injection objective substance into an injection target area, the syringe comprising:
   a syringe main body having a through-hole formed in an axial direction;
   a piston slidable in the through-hole;
   a syringe unit comprising a charging chamber configured to accommodate the injection objective substance, a plunger slidable in the charging chamber, and a nozzle portion including a flow passage having an inner diameter smaller than that of the charging chamber, the flow passage allowing the injection objective substance contained in the charging chamber pressurized by sliding movement of the plunger to flow therethrough, the nozzle portion configured to discharge the injection objective substance from a discharge port formed at a forward end of the flow passage, the syringe unit being detachably attached to a forward end side of the syringe main body, the charging chamber configured to receive a first amount of the injection objective substance before the syringe unit is attached to the syringe main body, the plunger configured to move toward the discharge port to define a second amount of the injection objective substance after the syringe unit is attached to the syringe main body and before the injection objective substance is injected into the injection target area; and
   a driving unit comprising an ignition device configured to combust powder, the driving unit configured to apply, via the piston to the plunger, discharge energy for discharging the second amount of the injection objective substance from the nozzle portion by the aid of a combustion product produced by the ignition device, wherein:
   the plunger has a rod portion extending toward the piston arranged in the through-hole of the syringe main body from an end surface disposed on a proximal end side in an attached state in which the syringe unit is attached to the syringe main body, the rod portion has an end disposed on the proximal end side;

the rod portion of the plunger is configured to be inserted into the piston in the attached state such that the end of the rod portion is accommodated without making contact with the piston; and an end surface of the piston disposed on the forward end side is configured to contact the end surface of the plunger disposed on the proximal end side so that the plunger is slidable toward the discharge port in a state in Which the rod portion is accommodated in an accommodating hole in the attached state, wherein the first amount is larger than the second amount, and wherein the syringe unit is configured to discharge a portion of the first amount of the injection objective substance by the movement of the plunger toward the discharge port before the powder combustion such that an amount of the injection objective substance to be injected into the injection target area is the same as the second amount.

2. The syringe according to claim 1, wherein:

the syringe main body is provided with a movement regulating portion configured to regulate movement of the piston toward the proximal end side in the through-hole; and the second amount of the injection objective substance is configured to be determined on the basis of a position determined by the movement regulating portion at which the piston can be moved most closely to the proximal end side in the through-hole.

3. The syringe according to claim 2, wherein:

the syringe main body has a first main body portion which is positioned on the forward end side and a second main body portion which is positioned on the proximal end side;

the first main body portion has therein a first through-hole which has a first predetermined diameter for allowing the piston to slide therein;

the second main body portion has therein a second through-hole which has a second predetermined diameter smaller than the first predetermined diameter for allowing a combustion product produced by the ignition device to arrive thereat; and a step, which serves as the movement regulating portion, is formed at a connecting portion between the first through-hole and the second through-hole when the syringe main body is formed by connecting the first main body portion and the second main body portion.

4. The syringe according to claim 2, wherein:

the ignition device is arranged on the proximal end side of the syringe main body;

the movement regulating portion is a cylindrical member which is arranged in the through-hole and which has an arrival space that extends in the axial direction so that the combustion product produced by the ignition device can arrive, a first end portion of the cylindrical member disposed on the proximal end side being fixed to a portion at which the ignition device is arranged, and a second end portion of the cylindrical member disposed on the forward end side being brought in contact with an end surface of the piston disposed on the proximal end side to thereby regulate movement of the piston toward the proximal end side; and an opening of the arrival space disposed on the forward end side is covered with the end surface of the piston disposed on the proximal end side in a state in which the movement of the piston toward the proximal end side is regulated by the cylindrical member.

5. The syringe according to claim 1, wherein:

the accommodating hole has a contact portion which makes contact with a side surface of the rod portion in the state in which the rod portion is accommodated in the accommodating hole and a non-contact portion which does not make contact with the side surface of the rod portion; and a deep portion of the accommodating hole is communicated with an opening of the accommodating hole via a gap formed between the non-contact portion and the rod portion in the state in which the rod portion is accommodated in the accommodating hole.

6. The syringe according to claim 1; wherein the rod portion has a length such that the end of the rod portion does not directly contact an inner wall surface of the accommodating hole when the plunger arrives at a deepest position located most deeply in the charging chamber.

7. The syringe according to claim 1, wherein:

the ignition device is an ignition device of an electric ignition type configured to combust powder based on a supply current supplied from outside;

a syringe assembly, comprising the syringe main body, the piston, the syringe unit, and the driving unit, is detachably attached to a syringe housing which has a power source unit configured to supply an ignition current to the ignition device; and an electric power supply terminal for the ignition device disposed on a side of the syringe assembly and an electric power supply terminal for the power source unit disposed on a side of the syringe housing are in a contact state when the syringe assernHy is attached to the syringe housing.

8. The syringe according to claim 1, wherein the rod portion is configured to be fully disposed within the accommodating hole when the injection objective substance is pressurized by the sliding movement of the plunger.

9. The syringe according to claim 1, wherein the syringe unit and the syringe main body are configured to be progressively connected to each other to define the second amount of the injection objective substance in the charging chamber.

10. The syringe according to claim 9, wherein the syringe unit and the syringe main body are configured to be connected to each other by thread-engagement.

11. The syringe according to claim 9, wherein the syringe unit and the syringe main body are configured to be progressively advanced until reaching a final screw-engagement position maintaining a direct contact state between the syringe unit and the syringe main body.

12. The syringe according to claim 9, wherein the syringe unit and the syringe main body are in direct physical contact with each other when the injection objective substance is pressurized by the sliding movement of the plunger.

13. A syringe for injecting an injection substance into an injection target area, the syringe comprising:

a syringe main body having a through-hole formed in an axial direction;

a piston slidable in the through-hole, a syringe unit comprising a charging chamber configured to accommodate the injection objective substance, a plunger slidable in the charging chamber to pressurize the injection objective substance contained in the charging chamber, and a nozzle portion configured to allow the pressurized injection objective substance to flow therethrough, the nozzle portion configured to discharge the injection substance via a discharge port formed at an end of the flow passage, the syringe unit being detachably attached to the syringe main body, the charging chamber configured to receive a first amount of the injection objective substance before the syringe unit is attached to the syringe main body, the plunger configured to move toward the discharge port to define a second amount of the injection objective substance after the syringe unit is attached to the syringe main body and before the injection objective substance is injected into the injection target area; and a driving unit comprising an ignition device configured to combust powder, the driving unit configured to apply, via the piston to the plunger, discharge energy for discharging the second amount of the injection substance via the nozzle portion based on the combusted powder, wherein the first amount is larger than the second amount, and wherein the syringe unit is configured to discharge a portion of the first amount of the injection objective substance by the movement of the plunger toward the discharge port before the powder combustion such that an amount of the injection Objective substance to be injected into the injection target area is the same as the second amount.

* * * * *